United States Patent
Ho et al.

(10) Patent No.: US 10,473,953 B2
(45) Date of Patent: Nov. 12, 2019

(54) TREATING OCULAR REFRACTIVE ERROR

(71) Applicant: Brien Holden Vision Institute Limited, Sydney (AU)

(72) Inventors: Arthur Ho, Coogee (AU); Padmaja Rajagopal Sankaridurg, Maroubra (AU); Earl Leo Smith, III, Houston, TX (US); Brien Anthony Holden, Kensington (AU)

(73) Assignee: Brien Holden Vision Institute Limited, Sydney, NSW (AU)

( * ) Notice: Subject to any disclaimer, the term of this patent is extended or adjusted under 35 U.S.C. 154(b) by 159 days.

(21) Appl. No.: 15/209,295

(22) Filed: Jul. 13, 2016

(65) Prior Publication Data

US 2016/0320634 A1    Nov. 3, 2016

Related U.S. Application Data

(62) Division of application No. 13/812,480, filed as application No. PCT/AU2011/000940 on Jul. 26, 2011, now Pat. No. 9,423,633.

(30) Foreign Application Priority Data

Jul. 26, 2010   (AU) ................................. 2010903334

(51) Int. Cl.
  *G02C 7/02*    (2006.01)
  *G02C 7/04*    (2006.01)
  (Continued)

(52) U.S. Cl.
  CPC .............. *G02C 7/042* (2013.01); *A61F 2/142* (2013.01); *G02C 7/02* (2013.01); *G02C 7/04* (2013.01);
  (Continued)

(58) Field of Classification Search
  CPC ........ G02C 7/024; G02C 7/045; G02C 7/081; G02C 2202/24; G02C 7/04; G02C 7/02;
  (Continued)

(56) References Cited

U.S. PATENT DOCUMENTS 5,151,723 A    9/1992 Tajiri
5,800,532 A    9/1998 Lieberman
(Continued)

FOREIGN PATENT DOCUMENTS

CN    101686801    3/2010
JP    2009/524085   6/2009
(Continued)

OTHER PUBLICATIONS

European Search Report dated Dec. 15, 2016 for EP 11811639.
(Continued)

*Primary Examiner* — Jordan M Schwartz
(74) *Attorney, Agent, or Firm* — Jones Day

(57) ABSTRACT

A lens for an eye that includes a zone with a first power profile for images received by the retina on the fovea, a zone with a second power profile for images received by the peripheral retina on the nasal side and a zone with a third power profile for images received by the peripheral retina on the temporal side. The first power profile is selected to provide clear or acceptable vision and the second and third power profiles are selected to affect the peripheral image position.

38 Claims, 8 Drawing Sheets

(51) Int. Cl.
*A61F 2/14* (2006.01)
*G02C 7/06* (2006.01)

(52) U.S. Cl.
CPC ............. *G02C 7/041* (2013.01); *G02C 7/045* (2013.01); *G02C 7/048* (2013.01); *G02C 7/06* (2013.01); *G02C 7/047* (2013.01); *G02C 2202/24* (2013.01)

(58) Field of Classification Search
CPC .......... G02C 7/041; G02C 7/042; G02C 7/06; G02C 7/047; G02C 7/048; A61F 2/1451; A61F 2/142
See application file for complete search history.

(56) References Cited

U.S. PATENT DOCUMENTS

| | | | |
|---|---|---|---|
| 6,045,578 | A | 4/2000 | Collins et al. |
| 6,234,629 | B1 | 5/2001 | Neadle et al. |
| 6,343,861 | B1 | 2/2002 | Kris et al. |
| 6,752,499 | B2 | 6/2004 | Aller |
| 7,025,460 | B2 | 4/2006 | Smith et al. |
| 7,665,842 | B2 | 2/2010 | Ho |
| 2003/0220631 | A1 | 11/2003 | Clapham |
| 2006/0001184 | A1 | 1/2006 | Phelan et al. |
| 2007/0159601 | A1 | 7/2007 | Ho |
| 2008/0062380 | A1 | 3/2008 | Phillips |
| 2009/0122264 | A1 | 5/2009 | Ho et al. |
| 2010/0036489 | A1 | 2/2010 | Lindacher et al. |
| 2010/0097570 | A1 | 4/2010 | Katzman et al. |
| 2010/0195044 | A1 | 8/2010 | Collins et al. |
| 2010/0296058 | A1 | 11/2010 | Ho et al. |
| 2011/0037944 | A1 | 2/2011 | Varnas |
| 2012/0140165 | A1* | 6/2012 | Artal Soriano .......... G02C 7/02 351/159.06 |
| 2015/0250583 | A1* | 9/2015 | Rosen .................. H05K 999/99 623/6.23 |
| 2017/0146824 | A1* | 5/2017 | Martinez .................. G02C 7/06 |

FOREIGN PATENT DOCUMENTS

| | | |
|---|---|---|
| NZ | 515069 | 6/2003 |
| RU | 2186417 C2 | 7/2002 |
| WO | WO 2000/059402 | 10/2000 |
| WO | WO 2003/009053 | 1/2003 |
| WO | WO 2006/004440 | 1/2006 |
| WO | WO 2007/082268 | 7/2007 |
| WO | WO 2008/116270 | 10/2008 |
| WO | WO 2009/034602 | 3/2009 |
| WO | WO 2009/055638 | 4/2009 |
| WO | WO 2009/129528 | 10/2009 |
| WO | WO 2010/103160 | 9/2010 |

OTHER PUBLICATIONS

English Translation of Search Report of Taiwan Patent Application No. 100126384 dated Aug. 20, 2015.
Vision CRC Limited, First Office Action, CN 201180045576.4, dated Sep. 28, 2014, 22 pgs.
Vision CRC Limited, International Search Report and Written Opinion, PCT/AU2011/000940, dated Aug. 24, 2001, 19 pages.
Lundstrom, L et al., "Peripheral Optial Erros and Their Change with Accommodation Differ Between Emmetropic and Myopic Eyes, Article 17" Journal of VI, Association for Research in Vision and Ophthalmology, US, vol. 9, No. 6, Jun. 29, 2009, pp. 1-11.
Ho, A et al., "Change in Peripheral Refraction and Curvature of Field of theHuman Eye with Accommodation", vol. 7163, Feb. 18, 2009, pp. 1-6.

* cited by examiner

TREATING OCULAR REFRACTIVE ERROR

RELATED APPLICATION

This application is a divisional of US application Ser. No. 13/812,480, filed 29 Mar. 2013, which is the National Phase application of International Application No. PCT/AU2011/000940, filed 26 Jul. 2011, which claims the benefit of Australian patent application 2010903334 filed 26 Jul. 2010. These applications, in their entirety, are incorporated herein by reference.

FIELD OF THE INVENTION

The invention generally relates to methods and devices for treating refractive error in an eye, Particular embodiments may have application to influencing the rate of progression of refractive error, by slowing the progression of refractive error and/or preventing the progression of refractive error. Particular embodiments may have application to the control of progression of myopia. Other embodiments may have application to the control of the progression of hyperopia.

BACKGROUND

Myopia (short-sightedness) is a disorder of the eye in which distant objects cannot be clearly focused, but near objects can be. Images of distant objects are brought to focus in front of the retina; that is, the focusing power of the eye is too strong 'at distance'. The condition may be corrected by the use of a negatively powered lens, which causes the distant Images to focus on or nearer the fovea. Myopia can be a serious and progressive condition that leads to increasing visual impairment despite the use of corrective lenses. It is becoming increasingly common, with some countries in South-East Asia reporting that 80% of children aged 17 years suffer from the condition.

Hyperopia (long-sightedness) is a disorder where distant objects can be focused, but near objects cannot be focused. Hyperopia may be corrected by the use of positive power lenses.

It is generally agreed that the process of normal eye development—emmetropization—is regulated by a feedback mechanism, which regulates the length of the eye to maintain good focus both at distance and at near or emmetropia. While it is also generally agreed that this feedback mechanism is somehow disturbed in eyes with refractive error, so that the eye grows too long In myopia and not long enough in hyperopia, there has not been consensus about the nature of the feedback mechanism or how the progression of myopia and hyperopia can be controlled. Both biochemical and optical (focal defect) mechanisms have been suggested.

While it is generally assumed that the feedback stimulus is somehow related to focal defects of the eye, the matter cannot be simple because, in progressive myopia, the condition may become worse—i.e., the eye continues to lengthen excessively—even though lenses that correct for distance vision are worn.

It has been proposed that an optical feedback mechanism is somehow upset by deficiencies in the accommodative effort of the eye due to excessive near work. The deficiency is considered to manifest as lag of accommodation (imprecise and insufficient accommodation) in some myopic eyes at near, resulting in defocus, which stimulates further undesirable axial elongation of the eye.

Bifocal lenses and PALS (progressive addition lenses) in spectacles have been proposed as a possible way to relieve the accommodative stress and defocus in the hope that the stimulus for elongation would be removed. U.S. Pat. No. 6,752,499 (Alter) describes prescribing commercially available bifocal contact tenses for myopic eyes that also exhibit near point esophoria to control the progression of myopia. Both concentric distance center and near center contact lenses were employed in myopic eyes with near point esofixation disparity. The zones of the concentric distance and near zones lie within the pupil.

In U.S. Pat. No. 6,045,578 (Collins et al.) it is proposed that emmetropization is regulated by the degree and direction of a spherical aberration present at the fovea. It is proposed that young myopes have higher levels of negative spherical aberration that promotes inappropriate eye growth and that the use of ophthalmic lenses to Impart positive spherical aberration will counteract axial growth and thus the progression of myopia.

In international patent publication number WO 200604440A2 (Phillips et al) it is proposed that defocus at the fovea for both distance and near vision inhibits the feedback stimulus for excessive eye growth. This publication proposes the use of a bi-focal contact lens that simultaneously provides the central retina with (a) clear vision for both distance and near and (b) myopic defocus for both distance and near. Again, the visual image will be degraded if this proposal is used.

U.S. Pat. No. 7,025,460 (Smith et al) describes the results of animal trials demonstrating that it is the optical state of the peripheral retina, not the fovea, that dominates the feedback stimulus for emmetropization. Thus, Smith et al, proposes that controlling off-axis focal points of the eye relative to the central on-axis focal points through manipulation of the curvature of field of the visual image provides a method of abating, retarding or controlling the progression of myopia and hypermetropia (impaired near vision caused by Insufficient eye length).

FIGS. 1 and 2 show how Smith et al describe an eye 1 that has a positive curvature of field. Since the central on-axis image point 2 is located in front of (i.e. opposite to the direction of light) the retina 3, this eye is considered myopic when measured using standard techniques such as auto-refractors, refractor-heads or trial frames, in the manner that eye-care practitioners are familiar. In this representative eye, the off-axis peripheral image points 4 for large field angles are located behind (i.e. in the direction of light) the retina 3. Thus the eye 1 of this example is relatively hypermetropic for the peripheral visual field. FIG. 2 shows a relative field curvature graph for the eye 1, which shows that the central to mid-peripheral field 5 is myopic (focus in front of retina 3) but the mid-peripheral to far-peripheral field 6 Is hypermetropic (focus behind retina 3).

FIGS. 3 and 4 show how the eye 1 of FIGS. 1 and 2 is prescribed an optical device 7 for the control of the progression of myopia, as described by Smith et al. This optical device 7 is designed so that it would generate a negative relative curvature of field 8 on the eye 1. The central, on-axis image 9 is focused sharply to the fovea 11 enabling good visual acuity. The optical device 7 introduces sufficient negative relative curvature of field 8 to focus the peripheral image points 13 more anteriorly, or in front (i.e. in the direction against the direction of light in the eye) of the retina 3.

U.S. Pat. No. 7,665,842 (Ho at al) describes providing one or more vision priority zones in which peripheral defocus or another aberration is corrected, with the lens also controlling the relative curvature of field for the peripheral retina in another region outside of the vision priority zone(s).

There remains a need for methods and optical devices that address the suggested optical (focal defect) mechanisms of progression of refractive error, particularly in relation to the progression of myopia.

SUMMARY

The present invention relates to the utilization of the finding that refraction in central and peripheral areas of the retina of human eyes, or at least the eyes of a substantial or significant number of people, is such that the natural curvature of field of the visual image is asymmetric around the visual axis of the eye. In more detail, the invention relates to the control of off-axis focal points of the eye relative to the on-axis focal points in an asymmetric manner through the use of an optical device that controls refraction of light for the eye.

For a patient with myopia, a method of treatment may therefore include measuring the refractive characteristics of the eye at the fovea (in other words on-axis or at the central retina) and outside the fovea (in other words off-axis or at the peripheral retina). The myopic patient may then be treated by modifying the refractive properties of the ocular system to provide clear or acceptable vision on-axis and to control the position of the image at the peripheral retina, for example to move the image onto or in front of the retina. For an eye with asymmetry in the peripheral retina, a device to move the image at the peripheral retina will require different refractive powers to treat the asymmetry observed in different parts of the peripheral retina. For a patient with hyperopia, the peripheral images may be moved onto or behind the retina, again treating for observed asymmetry in the eye.

One way of modifying the refractive properties is through the use of a lens. Embodiments of a device for an eye include contact lenses, spectacle lenses, corneal implants or other lenses that have different power profiles for images received by different parts of the peripheral retina. The class of contact lenses includes lenses that operate by having a refractive power and orthokeratology lenses that achieve a change in the refractive properties of the eye by reshaping the cornea.

In some embodiments a lens is provided for affecting the progression of myopia or hyperopia in an eye. The lens comprises a nasal optic zone and a temporal optic zone for refracting light to be received by the peripheral retina. The nasal optic zone and temporal optic zone have different refractive powers. The lens may further include a central optic zone with a refractive power to correct for the refractive power of the eye on-axis and to provide clear or acceptable distance vision at all distances.

The lens may therefore comprise regions for affecting light destined to various sectors of the retina in a rotationally asymmetric manner relative to the central on-axis focal points. The lens may affect the peripheral light rays received by the retina of the patient's eye in any given sector so that their focal points are on or anterior to the surface of the retina for myopes, or on or posterior to the surface of the retina for hyperopes. In this way, for at least some patients, the stimulus for aberrant eye growth may be removed in substantially all sectors or over an increased amount of the retina. The removal of stimulus may be performed especially in those regions deemed to be of most importance for inhibiting such eye growth.

In some embodiments a method of prescribing an optical device for affecting images received by the peripheral retina includes observing whether the recipient of the optical device has a symmetrical or asymmetrical curvature of field. The prescribed optical device may then either treat the peripheral image symmetrically or asymmetrically dependent on the observation.

DESCRIPTION

Figure 5:
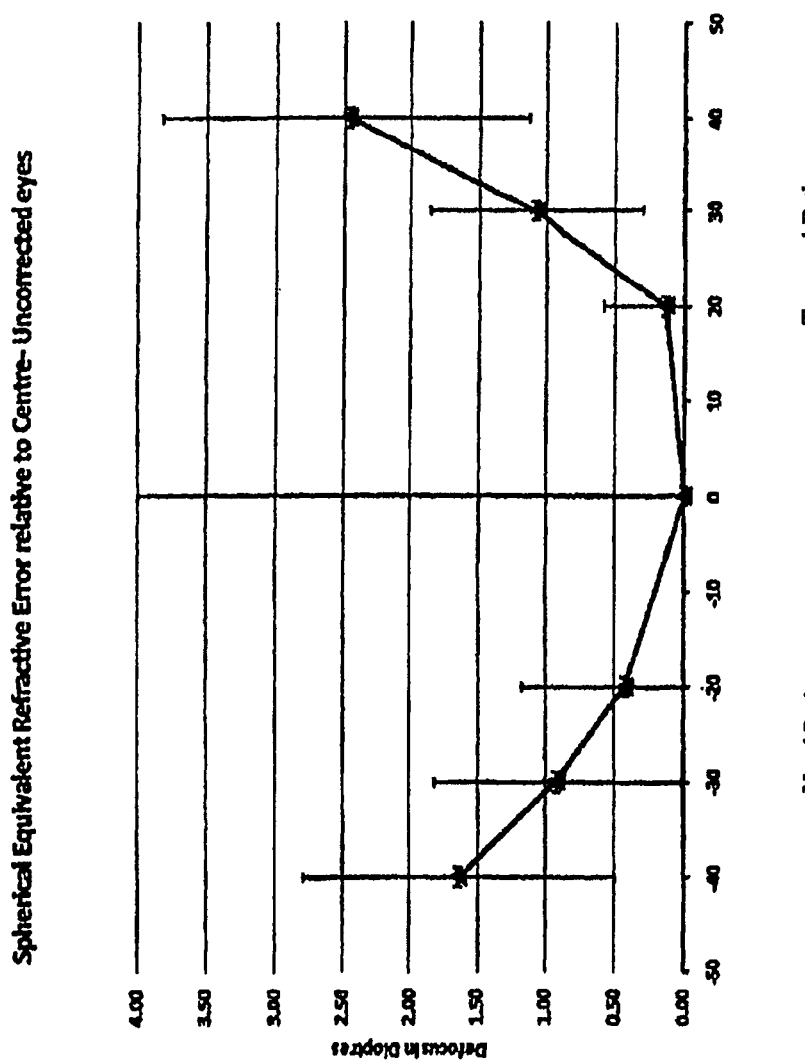
FIG. 5 shows a plot illustrating the asymmetry in the nasal versus temporal peripheral retina for a sample group of eyes of children with myopia.

FIG. 5 shows a plot of the refractive state for 1155 eyes of children with myopia at the peripheral retina in the horizontal meridian, with measurements for the both the nasal and temporal quadrants taken. The horizontal (independent) axis indicates the peripheral angles at which measurements were taken. Measurements at the nasal retina represent the temporal visual field and measurements at the temporal retina represent the nasal visual field. The vertical (dependent) axis is the amount of defocus of the light rays at the retina, in diopters (D), relative to the amount of defocus along the visual axis of the eye. Accordingly, positive values Indicate relative hyperopic defocus and negative values relative myopic defocus. Measurements of defocus were taken on axis and at 20, 30 and 40 degrees from the optical axis, both temporally and nasally. The eyes had a spherical equivalent refractive error of $-2.27 \pm 0.81$D on axis. All measurements were taken using an open field Shin Nippon autorefractor utilizing head-turn for off-axis measurements so the eyes were in the primary position for all measurement angles. The plot was completed by simple straight line interpolation between the measured points.

FIG. 5 shows that at 20 degrees, the nasal retina is experiencing 0.43 D of hyperopic defocus relative to central retina. In contrast, the temporal retina is experiencing only 0.14D of hyperopic defocus relative to the central retina. At 30 degrees, the amount of hyperopic defocus experienced by the nasal retina increases to 0.92D relative to central retina and the temporal retina experiences 1.08D. At 40 degrees, the hyperopic defocus experienced by the nasal retina increases to 1.64D compared to central retina. At the temporal retina, there is a significant increase in the hyperopic defocus and increases to 2.47D relative to central retina.

FIG. 5 shows that whilst there may be relative hyperopic defocus experienced at both the nasal and temporal retina relative to the central retina, the amount of defocus experienced at each point measured varies and is asymmetric around the central on axis image point. FIG. 5 also shows the standard deviation of the measured relative defocus at each measurement angle for the same set. For some eyes in the sample set, the asymmetry was such that there was relative myopic defocus on one side of the peripheral retina and relative hyperopic defocus on the other side.

The measurement of the eye, as represented by the plot in FIG. 5 differs substantially from the representation described in U.S. Pat. No. 7,025,460 (Smith et al), which assumes the curvature of field of this eye is rotationally symmetric relative to the central on-axis image point. Thus, the manipulation of the curvature of the field in a symmetric fashion, as taught in U.S. Pat. No 7,025,460 (Smith et al), is unlikely to eliminate the defocus in all quadrants of an eye having characteristics shown in FIG. 5 and may be under-correcting or over-correcting for either the hyperopic or myopic defocus present in at least some locations of the peripheral retina.

Figure 4:
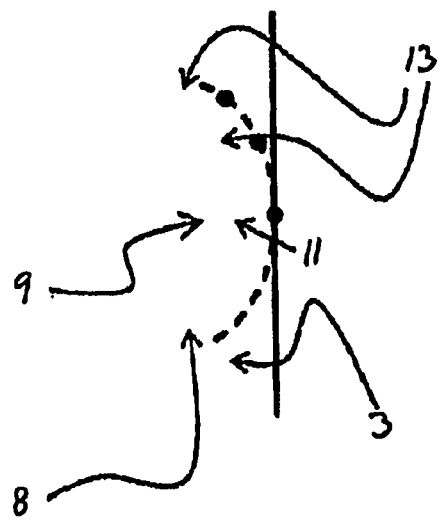

Accordingly, the present invention involves modifying the wavefront of light received by an eye by creating an ocular system including the eye that takes into account asymmetry in the curvature of field of the eye to be treated. In other words, if the relative curvature of field was controlled in a symmetrical manner, then the peripheral image would remain asymmetrical, however if the asymmetry of the eye is taken into account, this asymmetry can be reduced or eliminated. This allows placement of the image substantially on the retina on both the nasal and temporal sides of the fovea. Alternatively, this allows the substantially symmetrical profile shown in FIG. 4 to be achieved for a myopic eye, despite asymmetry in the refractive characteristics of the eye for peripheral images. Similarly, for a hyperopic eye, taking account of the asymmetry can result in a treated eye having substantially symmetrical characteristics or at least reduced asymmetry.

FIGS. 6 to 9 show examples of the general structure of four different contact lenses 100, 200, 300, 400, for controlling the relative position of peripheral images of an eye with asymmetric relative curvature of field in the horizontal direction. Each lens is for a left eye and generally has a different refractive power in a region on the nasal side to that on the temporal side. A design for the right eye may be mirror image in structure, but the power profile in each optic zone will be selected dependent on the characteristics of the right eye. Each lens has an optic zone 101, 201, 301, 401, which may be between approximately 6 to 8 mms in diameter, depending on the particular implementation. Outside the optic zone 101, 201, 301, 401 is a carrier portion 102, 202, 302, 402, which provides stability for the lens when applied to the eye. The carrier portion may for example extend for another 4 to 6 mm, so that the total lens diameter up to the lens edge 106, 206, 306, 406 may be about 12 mm. Other embodiments may have differing dimensions, and particular dimension lenses may in some cases be selected according to the eye to which the lens is to be applied, for example to reflect differences in size of the pupil 50. In FIGS. 6 to 9 the outer periphery of the carrier zone is represented in dashed lines.

The lenses are each oriented on the eye with the utilization of a suitable lens stabilization technique. The requirement to stabilize the orientation of the lens arises since the power of the contact tens varies across the surface and is effected to ensure application of power to selected regions of the central and the peripheral regions of the retina. The lenses may be stabilized on eye with a lens stabilizing mechanism selected from a prism ballast, double slab-off and truncation.

For the representative eye plotted In FIG. 5, between the field angles of 20 to 40 degrees, the temporal peripheral retina is experiencing 0.14 to 2.4D of relative hyperopic defocus and the nasal peripheral retina is experiencing 0.43 to 1.64D of relative hyperopic defocus. The following description of the lens structures shown in FIGS. 6 to 9 assumes that the power profile of the optic zones in the contact lens is designed with this defocus, in mind.

Figure 6:
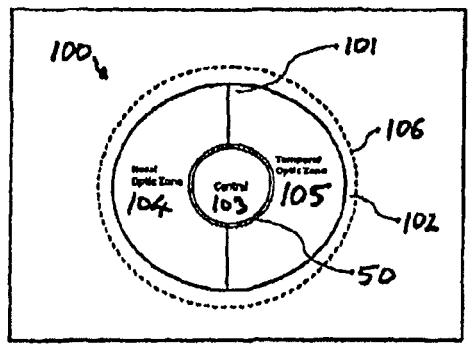
FIGS. 6 to 9 show example structures of a contact lens for eyes with asymmetry between the nasal and temporal fields.

In the example shown in FIG. 6, the lens 100 has a disc-shaped central optic zone 103. The central optic zone 103 has a diameter selected from the range of from about 0.5 mm up to about 3 mms. The central optic zone 103 is located and provided with a power to correct for the central refractive error of the eye (measured at the fovea). With this selection of power, the central optic zone 103 allows for clear vision at all distances (assuming that the eye can accommodate to provide in focus near vision). The power profile of the lens varies between the nasal optic zone 104 and temporal optic zone 105 on either side of the central optic zone 103. The power in these zones is selected to correct for the defocus measured In the temporal and nasal quadrants of the peripheral respectively.

In some embodiments, these zones may carry a single power that corrects for the average defocus measured at the peripheral retina over a range of field angles. Thus for example, in these embodiments the nasal optic zone 104 will correct for the mean 1.23D of relative hyperopic defocus experienced by the peripheral retina on the temporal side and thus will be 1.23D relatively more positive compared to the power of the central optic zone 103. Similarly, the temporal optic zone 105 will correct for the mean 0.99D of relative hyperopic defocus experienced by the peripheral retina on the nasal side and thus will be 0.99D relatively more positive compared to central optic zone power.

In other embodiments, the nasal and temporal optic zones 104, 105 carry a plurality of powers, selected with regard to the defocus measured at two or more locations of the peripheral retina. For example, the power of the nasal optic zone may be set taking account of the relative defocus experienced by the temporal peripheral retina at 20, 30 and 40 degrees and include a smooth transition between the powers required at these angles. If measurements are taken for an eye at more angles or at only two angles, then the power may be set in the nasal and temporal optic zones 104, 105 having regard to those measurements. The variation may reflect the measured curvature of field of the eye to which the lens is to be applied. For example, a lens may be selected with a power profile across the nasal optic zone 104 that has the objective of a substantially constant distance (which may be zero) between the focal point and the retina. Similarly variations in power may occur across the temporal optic zone.

Figure 7:
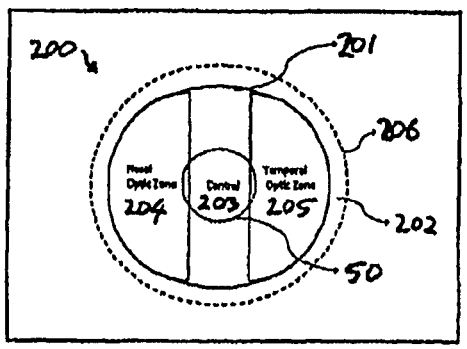
Figure 8:
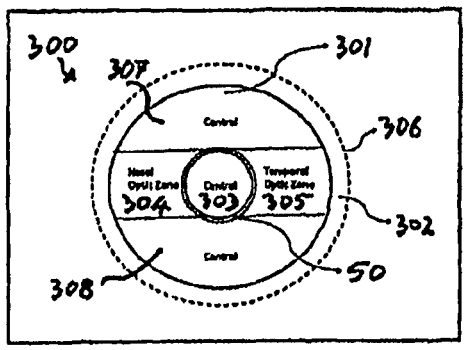
Figure 9:
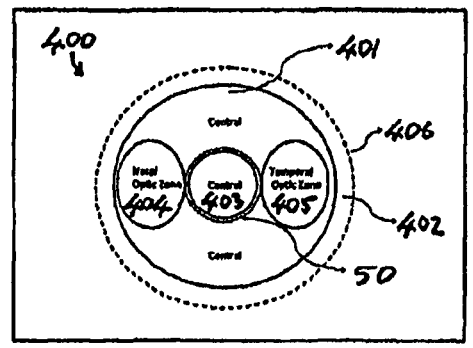

The options of having either a single power in a zone or a varying power in a zone also applies to the lens structures shown in FIGS. 7 to 9.

In the example shown in FIG. 7, the lens 200 has a central optic zone 203 extending along the vertical meridian of the lens 200. The central optic zone 203 has a constant power from the centre to the periphery of the optic zone in both directions. The width of the meridian is in the range from about 0.5 mm to about 3 mms. The power profile of the lens 200 varies between the nasal optic zone 204 and temporal optic zone 205 on either side of the central zone 203 and will correct for the defocus measured for the peripheral retina on the temporal and nasal sides respectively, as described for the example shown in FIG. 6.

In the example shown in FIG. 8, the lens 300 has a central optic zone 303 between approximately 0.5 mm to 3 mm in diameter with a refractive power selected to correct for the central refractive error of the eye. In the horizontal meridian, the power profile of the lens 300 varies between the nasal and temporal optic zones 304, 305 on either side of the central optic zone 303, as described for the example shown in FIG. 6. The nasal and temporal optic zones 304, 305 have a height of approximately 0.5 mm to 3 mm, which may be selected to match the diameter of the central optic zone 303, although in other embodiments the height of these zones may be more or less than the diameter of the central optic zone 303. The nasal and temporal optic zones 304, 305 both extend from the central optic zone 303 to the edge of the optic zone 301 of the lens 300. The central optic zone 303 is extended into the regions 307, 308 outside of the peripheral optic zone. In other words, in this example, in the optic zone 301, the lens 300 has a power selected to correct for the central refractive error of the eye in all regions outside of the nasal and temporal optic zones 304, 305.

In the example shown in FIG. 9, the lens 400 has a central optic zone 403 between approximately 0.5 to 3 mm in diameter that corrects for the central refractive error. In the horizontal meridian, the power profile of the lens varies between the nasal and temporal optic zones 404, 405 on either side of the central optic zone 403. The nasal temporal zone 404 and temporal optic zone 405 correct for the defocus measured in the temporal and nasal quadrants of the peripheral retina respectively, as described above with reference to the example shown in FIG. 6. Both the nasal and temporal optic zones 404, 405 have an oblong shape of width of about 3.0 mm to 5.0 mm. These zones need not be oblong and could be other shapes, like circular or substantially rectilinear. The remainder of the lens carries the same power profile as the central optic zone.

For each of the examples shown in FIGS. 6 to 9, there may be a transition zone connecting the central optical zone (and any other region with the same power profile as the central optic zone) to the peripheral optic zones (consisting of the nasal and temporal optic zones). The transition zone is at the boundary of the central and nasal or temporal optic zones and can vary in width from about 0.25 mm to about 1.0 mm. The transition zone bridges the difference in power profile and In some embodiments is shaped to provide a smooth curve transition between the zones. In other embodiments, there may be a point on the lens where the central optical zone finishes and the peripheral optic zone commences.

As will be appreciated from the description herein, including but not limited to the examples shown in FIGS. 6 to 9, the shape and layout of the optic zones in a contact lens may be varied substantially, creating a large range of different embodiments. By way of example; the central optic zone 103, 203, 303, 403 may be asymmetrical about a vertical meridian of the lens through the centre of the lens. This asymmetry may reflect a low rate of change in the curvature of field for one side of the peripheral retina. Referring to FIG. 5, the rate of change between zero to twenty degrees for the temporal retina is low, so that some embodiments of lens may have a power selected to correct on-axis vision for these field angles. If the eye already has the desired or an acceptable curvature of field on one side, the central optic zone may be extended to encompass the entirety of what would otherwise be the temporal optic zone (or the nasal optic zone). Each embodiment however remains characterized by different power profiles in a nasal optic zone and a temporal optic zone, selected to control the off-axis focal points of the eye relative to the central on-axis focal points in an asymmetric manner.

The lens power profile may not consider the refractive error state of the eye in the vertical direction, as differences along vertical meridians are not considered as important. However, in other embodiments, the refractive error state of the eye in the vertical direction may also be corrected, in the same way as described herein for the horizontal direction. In other words, the relative curvature of field naturally occurring In the eye in the vertical direction may also be measured and the lens may include upper and lower optic zones to control the curvature of field for the lower and upper potions of the peripheral retina respectively. Where there is asymmetry in the vertical direction, this may be accounted for in the same manner as asymmetry in the horizontal direction. Where both the horizontal and vertical directions are controlled, the peripheral image will be controlled in all quadrants of the eye.

The examples shown in FIGS. 6 to 9 show a central optic zone 103, 203, 303, 403. In the examples, a central optic zone of diameter or width of about 0.5 to 3.0 mm is provided. The size of the central optic zone may be selected regarding to the pupil diameter of the recipient of the lens or having regard to the average pupil diameter of a population sample most representative of the recipient or a sample representing the general population. Generally, a larger central optic zone allows for clearer vision, particularly if the central optic zone has a constant or substantially constant power profile across the area of the pupil. However, a lens with a smaller central optic zone may be required for some recipients where control of peripheral defocus close to the fovea is needed. Some sacrifice of on axis image quality may then result.

Also, the central optic zone 103, 203, 303, 403 may have a power profile selected to correct on-axis vision, with a substantially uniform power across its diameter In all directions. Having a central optic zone may be advantageous in minimizing defocus of the image received by the fovea. In other embodiments, the power profile of the central optic zone may be allowed to vary to some extent. For example, the lens may be designed to have a power profile that progressively changes from the centre point of the lens out to the nasal and temporal optic zones. The power at the centre point of the lens may be selected to correct on-axis vision, or selected to provide substantially clear vision on axis.

The contact lenses shown in FIGS. 6 to 9 may be silicone hydrogel lenses, rigid lenses, scleral lenses or hybrid lenses. Similar lens designs may be made for spectacle lenses and corneal implants. For both these types of lenses the carrier portion is not required. A suitable structure for spectacle lenses may be that shown in FIG. 9, except with a central optic zone of a width of about 8 to 20 mm. Some embodiments of spectacle lens may have a large transition zone between the central optic zone and the peripheral optic zone, so as to avoid visible lines on the lenses and to reduce interference with the clarity of vision of the wearer when their eyes are not directed straight ahead. Corneal implants will be shaped to create a conreal surface profile that results in the refractive characteristics described. An orthokeratology lens may similarly reshape the cornea to achieve the relative curvature of field required for the peripheral retina.

A collection of lenses may be provided from which a selection is made for individual recipients. For example, for each power in the central optic zone, there may be a selection of asymmetric peripheral optic zones. The selection may be made with reference to a population norm and the deviation for the population, for example as represented in FIG. 5. Where there a significant variations in classes of recipients, different population norms may be constructed for each class. The number of selections for each power in the central optic zone may vary. One example may be a selection of: one for the average for the population four for the standard deviation either side (which takes into account that a eye with relatively more myopic defocus in comparison to the norm on one side of the peripheral retina may my more myopic or more hyperopic in comparison to the norm on the other side of the peripheral retina) and another four at 1.5 standard deviation. Additional lenses may be available for one or more of: 0.25 of the standard deviation, 0.5 of the standard deviation, 0.75 of the standard deviation and 2.0 standard deviations. It will be appreciated that some of the lenses In the collection may be symmetrical or substantially symmetrical, which may be selected for appropriate recipients. There may be selections for the power profile of the central optic zone and/or the structure (for example two of more of the structures shown in FIGS. 6 to 9) as well.

Figure 10:
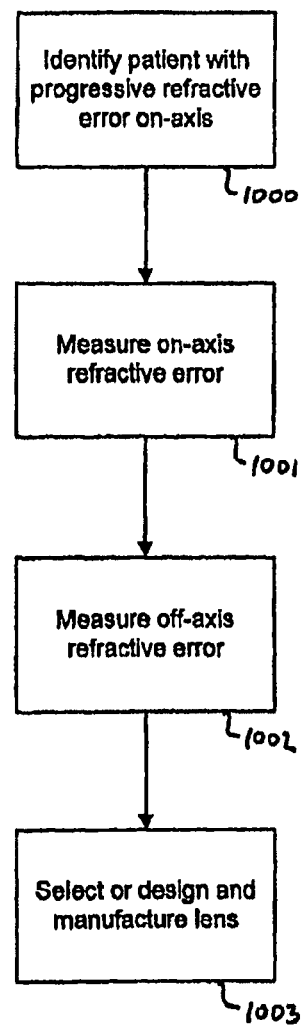
FIG. 10 shows a flow chart of a method for treating an eye with an optical device including a lens.

FIG. 10 shows a flow diagram of a series of steps for prescribing a lens for the correction of refractive error of an eye with the purpose of also attempting to control the change in refractive error over time. In step 1000 a patient is identified with refractive error. This identification step may be achieved by a simple examination of the history of on-axis refractive error of a patent, for example over the past 6 months or 1 to 3 years, or longer. Alternatively, the Identification step 1000 may be replaced with identification of a patient that has refractive error without reference to any history of error or its progression.

In step 1001 the on-axis refractive error is measured. This measurement is used to identify the required correction on-axis. For example, the patient may be measured as having refractive error of −3 D, in which case the central optic zone of the lens, for example the central optic zone 103, 203, 303, 403 shown in FIGS. 8-9 is selected to have a power to correct this error.

In step 1002 the off-axis refractive error is measured. Measurements are taken for off-axis field angles nasally and temporally. As previously described, variation in field of curvature for vertical angles may be ignored, but may be measured and included in the lens design if required. Step 1002 may comprise taking a measurement at a single angle in the nasal and temporal directions, for example at 30 degrees relative to the on-axis direction. Alternatively, step 1002 may comprise taking measurements at more than one angle in the nasal and temporal directions. For example two measurements may be taken at 15 and 30 degrees, three measurements taken at 15, 30 and 35 degrees or six measurements taken at 5, 10, 15, 20, 25 and 30 degrees. The angle need not be a multiple of five, these angles being described for illustrative purposes only. More than one measurement may be taken at a single angle and these may be combined, for example through averaging or otherwise or may be subject to evaluation, for example with reference to the position of the eye when the measurement was taken, with the measurement expected to be the most accurate selected.

Depending on the instrument used, step 1002 may include separate steps for measuring the refractive characteristics of an eye at each required angle relative to the optical axis of the eye. For example, this may be required if the patient has to be physically moved or asked to move their line of sight, or if the instrument needs to be physically moved relative to the patient's eye to obtain the measurements.

In step 1003 the measurements are compared to available lenses with differing power across the horizontal meridian for the best match, or a new lens design is formed for manufacture with the required power profile for the eye. The power profile corrects for the on-axis refractive error measured in step 1000 in the central optic zone and has a power selected with regard to the refractive characteristics of the eye in the nasal and temporal peripheral regions.

For example, the power profile may be selected to place the image of peripherally viewed objects on the retina in both the nasal and temporal directions, or on the retina for at least those angles which have been measured in step 1002. Alternatively, where there are constraints on the power profile across the lens, the power profile may be selected to place the image of peripherally viewed objects as close as possible to the retina within those constraints. The constraints may include a constraint on the maximum rate of change or constraints due to requirements to correct other conditions, such as astigmatism.

Alternatively, the power profile may be selected to place the image of peripherally viewed objects at another position relative to the retina, where that is viewed as potentially providing benefit. For example, for a myopic eye, the power profile may be selected to place the image of peripheral objects in front of the retina. For a hyperopic eye, the power profile may place the image of peripheral objects behind the retina. The objective for placement of the image of peripheral objects need not be symmetrical—for example the lens for a myopic eye may place the peripheral image on the temporal side on the retina and the peripheral image on the nasal side in front of the retina.

The refractive state of the eye, both on-axis and for peripheral objects, is measured using retinoscopy. Either manual or autorefractors may be used to take the measurements. An example of an instrument specifically designed for measuring both on axis and peripheral refraction will now be described.

Figure 1:
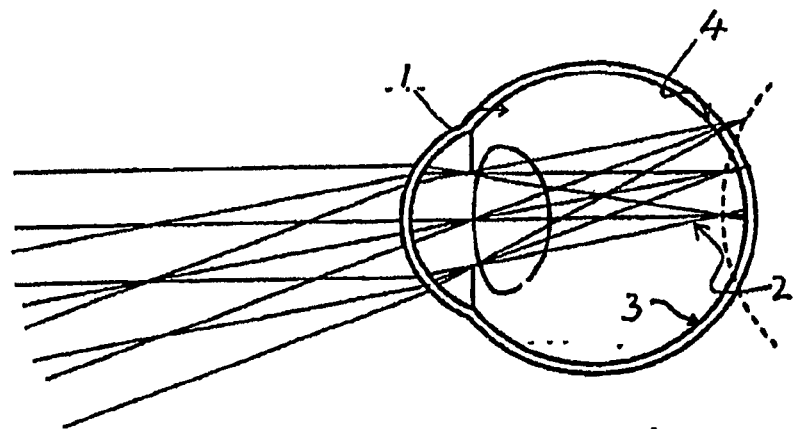
FIGS. 1 and 2 (prior art) show a previous diagrammatic description of an eye with positive curvature of field.
Figure 2:
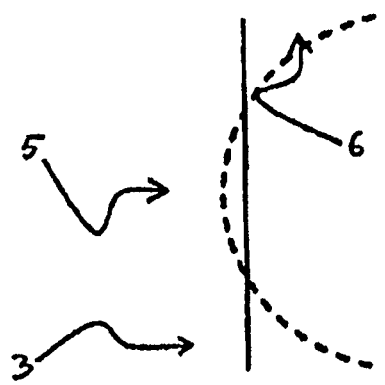
Figure 11:
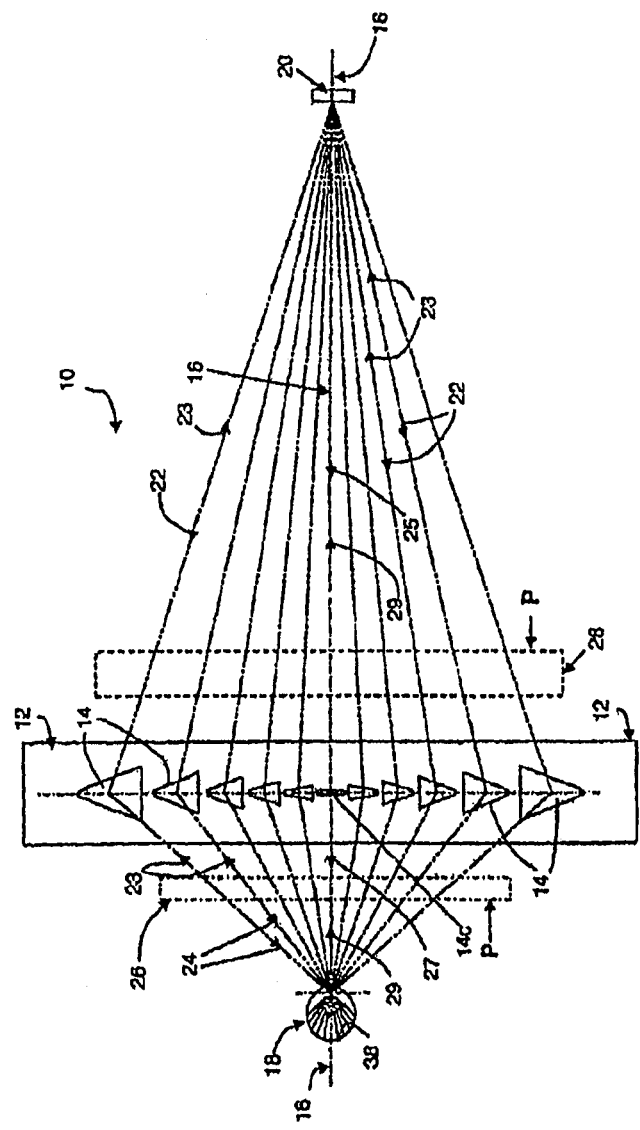
FIGS. 11 to 13 show an instrument for obtaining on-axis and off-axis refractive measurements of an eye.
Figure 12:
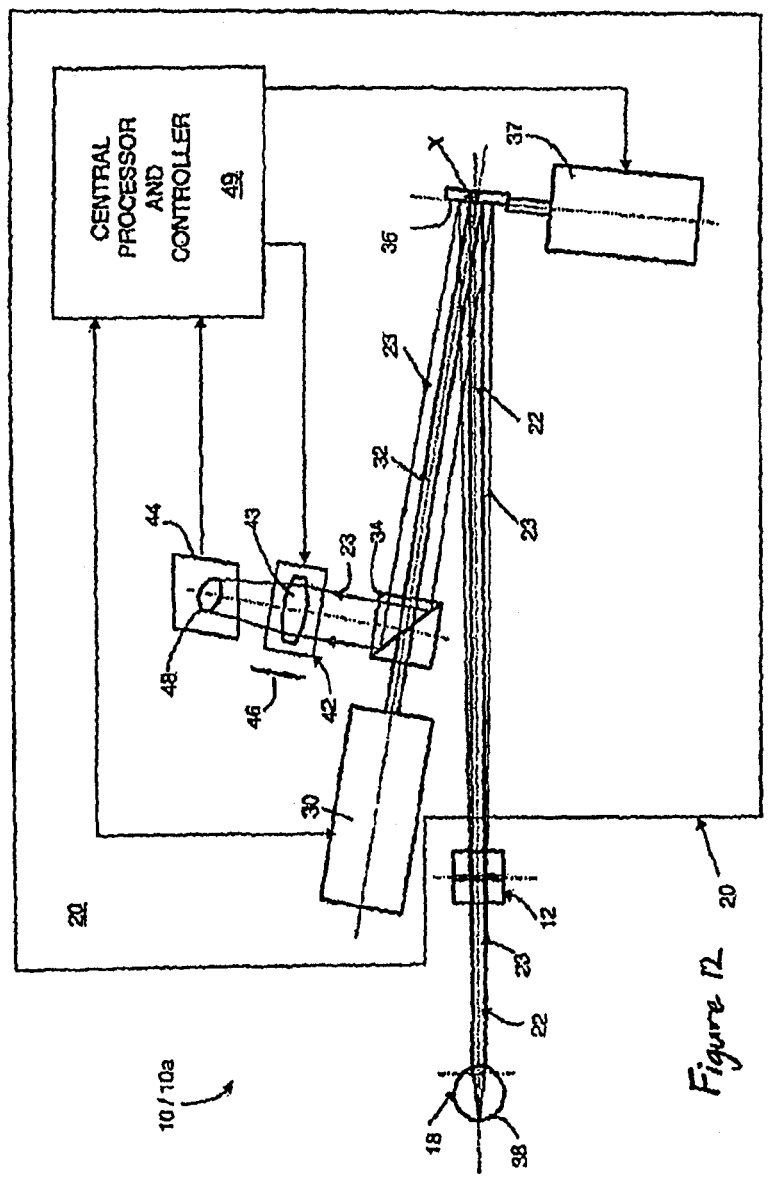

FIGS. 11 and 12 show an instrument 10 suitable for measuring peripheral refraction, determining the amount of decentration and applying a correction factor to obtain a corrected measurement of peripheral refraction. The present invention may be implemented In software in the controller 49 (see FIG. 12). The apparatus, together with possible variations of the instrument 10 and alternative apparatus that may be adapted to implement the current invention is described in international patent publication PCT/AU2008/000434, published as WO 2008/116270 A1, the content of which is incorporated herein in its entirety by reference. The instrument 10 uses the general methodology of 'instrument rotation' described in relation to FIG. 2. Other instruments with which the present may be implemented may use the 'eye turn' or 'head turn' methodologies.

Figure 3:
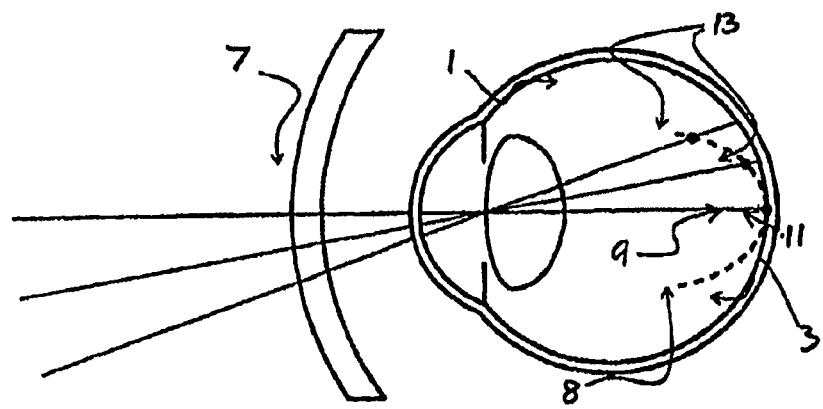
FIGS. 3 and 4 (prior art) show how the curvature of field of the eye represented by FIGS. 1 and 2 may be manipulated using an optical device.

FIG. 11 shows the basic layout of the instrument 10. An array 12 of deflector elements 14 is in this example instrument a linear row that extends symmetrically and laterally on either side of the optical axis 16 of the eye-related optical system 18 under investigation. It will be assumed that system 18 is the eye of a patient with or without the addition of prosthetic lenses or other modifications. An illuminating light source, controlling processor and return-beam detector are indicated by a single undifferentiated unit 20 arranged on axis 16, which is described In more detail with reference to FIG. 3. Unit 20 directs illuminating beams, indicated by arrow heads 22, to array elements 14 to generate a corresponding set of interrogating beams, indicated by arrow heads 24, that are directed into eye-system 18 at different peripheral angles relative to axis 16. A return beam, indicated by arrow heads 23, is generated by each interrogating beam 24 and is directed back to unit 20 via the respective element 14 for detection. It is convenient for illuminating beams 22 to be directed in sequence from one element 14 to the next to thereby sequentially generate the interrogating beams 24 and return beams 23.

In this example, a central illuminating beam, a corresponding central interrogation beam and a corresponding central return beam are indicated by arrow heads 25, 27 and 29. Also in this example, each deflector element is a prism (except central element 14*c*) that has an apex angle such that each interrogation beam 24 is directed into eye 18 and each return beam 23 is directed to unit 20. Central element 14*c* is effectively a null element that does not deflect the illuminating beam; it may be a parallel-sided plain glass as shown, but that is not even necessary. Also in this example, array 12 is substantially linear so that interrogating beams 24 and 27 are substantially co-planar allowing one meridian—the horizontal In this example—of system 18 to be investigated. Non-horizontal meridians of the system can be investigated by simply rotating the instrument 10 about optic axis 16 relative to eye 18.

The transmission of Interrogating beams 24 and 27 one at a time into eye 18, and the generation of a corresponding sequence of return beams 23 and 29, can be effected in a variety of ways. First (as will be described below), unit 20 may include a beam scanner that directs a single narrow illuminating beam from one element 14 to another. Second, multiple elements 14 can be illuminated at one time and interrogating beams 24 and 27 can be gated to effect scanning of eye 18 and the generation of a sequence of return beams 23 and 25. This can be done by, for example, inserting an electronically controllable LCD shutter 26 between array 12 and eye 18 and using it as scanning means by which interrogating beams 24 from prisms 14 are admitted into eye 18 one at a time. Third, a similar shutter 28 may be inserted between array 12 and unit 20 to gate illuminating beams 22 and 25 to illuminate one or more elements 14 at a time. Thus, it is not essential for unit 20 to include scanning means and it is possible to distribute the scanning function between scanner means in unit 20 and shutters such as indicated at 26 and/or 28

In this way, successive interrogation/return beam pairs diverge/converge at successively larger/smaller angles with respect to axis 16 as they pass into and out of eye 18. Sequential scanning from one angle to the next adjacent will probably be most convenient but many other scan sequences may be used to minimise biases that might arise due to fixed sequential scanning. While illumination of more than one beam deflector element 14 at a time can easily be achieved by use of a scanner in unit 20, it is then necessary to distinguish the multiple simultaneous return beams that will result. This can be done by using shutter 26 or 28 as a beam-chopper or selective polariser to differentially encode each return beam that needs to be distinguished from another at the detector.

FIG. 12 is a more detailed side elevation of instrument 10 of FIG. 11 in which the principal components of unit 20 are shown separately. A light source 30 directs a collimated source beam 32 via a beam-splitter 34 to an oscillating mirror scanner 36 that is moved by actuator 37 to generate illuminating beams 22. The illuminating beans 22 are scanned from deflector to deflector in array 12 to generate the sequence of interrogating beams 24 that are directed into the eye-system 18 and onto the retina 38 over the desired range of incident angles. Scanning mirror 36 thus forms a point source or common point for beams 24 and a common point (indicated at X) for all return beams. Thus, each return beam 23 returned from retina 38 passes back via deflector array 12 and scanner mirror 36 to beam-splitter 34 by which it is diverted via a focusing system 42 to a photo detector 44. System 42 includes a moveable lens assembly 43 that can be moved axially back and forth through a focus range, as indicated by arrows 46. While the source beam 32 (and, thus, the illuminating, interrogating and return beams 22, 24 and 23) can have any desired spot, disc or annular cross-section desired, an annular cross-section like that commonly used in known autorefractors (such the Shin-Nippon SRW-5000 mentioned above) is preferred as it can be analysed and processed in a substantially standard manner.

Each return beam 23—or more correctly its image 48 at detector 44 thus contains information of the (uncorrected for decentration) refractive status of the eye-system that is captured or quantified by the photo detector 44, which is preferably a two-dimensional array of photo sensors. The photo detector 44 also captures an image of the pupil corresponding to the image shown in FIG. 7 for the determination of the decentration of the illuminating beams 22. An image of the pupil is captured when each refraction measurement is made, so that there is one image for each illuminating beam 22. This allows the refraction measurement to be individually corrected at each incident angle, dealing with relative movement of the eye-system 18 and the measurement axis between measurements.

The unit 20 includes a central processor and controller 49 that may conveniently comprise a dedicated PC and is connected to accept and analyse the output of detector 44 and to drive lens assembly 43 under servo-control. Processor 49 is also connected to control scanner driver 37 and to ensure correct timing of illumination and return signal detection. A connection between light source 30 and processor 49 is also shown as it will be convenient to ensure that source beam 32 is correctly configured and that a representation of the current source beam sectional pattern is stored for comparison with image 48.

While each return beam 23 is being received, focusing lens assembly 42 is moved along the direction of the optical axis to vary the focus size and shape of the image 48. Commonly, three positions of the focusing assembly 42 are recorded for each of three return beam image shapes: one position where the image (spot or ring) appears smallest and in sharpest focus, a second position where the image appears maximally elongated in one meridian and a third position where the image is maximally elongated in a different meridian, usually one that is orthogonal to the first meridian. The three positions of lens assembly 42 respectively indicate the spherical equivalent power of the eye, the sagittal astigmatic component and the tangential astigmatic component of the refraction. The significance of spot/image size in relation to spherical equivalent power of eye 18 can be understood in the following elementary way. Since the interrogating beam 24 that enters eye 18 is collimated, a normal or emmetropic eye will return a parallel collimated beam, a myopic eye will return a convergent beam and a hyperopic eye will return a divergent beam, both of which will result in larger images sizes.

The central processor and controller 49 stores in memory the correction algorithm, either as a function or as a look-up table. It also includes instructions to receive and/or automatically determine the decentration and to apply the correction algorithm to the measured refraction values to calculate a corrected refraction value. The corrected refraction values may then be stored, displayed or communicated to another device.

Figure 13:
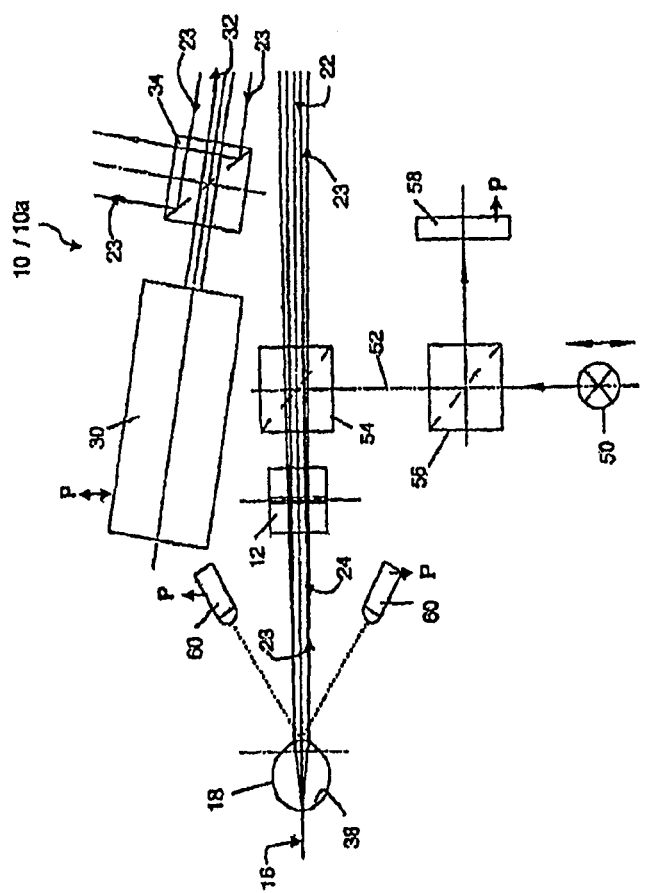

FIG. 13 shows some features that may be added to enhance the performance of the instrument 10 of FIGS. 13 and 14. A movable fixation target 50 is located on a gaze beam path 52 that is optically coupled by a first additional beam-splitter 54 into return beam path 23 and on optical axis 16. Fixation target 50 aligns the gaze or axis of the eye with optical axis 16 of the system and controls accommodation. A second additional beam-splitter 56 In gaze path 52 directs an image of eye 18 onto a CCD detector 58, allowing gaze direction and eye-alignment to be monitored since CCD detector 58 receives the ocular image via beam-splitters 54 and 56. Optical or acoustical distance sensors 60 can be used to (alternately or additionally) indicate when eye 18 appears to be axially aligned. Sensors 60, along with detector 58 if desired, can be connected to processor 49 (FIG. 12)—as indicted by arrows marked P—so that initiation of a measurement cycle can be automatic.

It will be understood that the invention disclosed and defined in this specification extends to all alternative combinations of two or more of the individual features mentioned or evident from the text or drawings. All of these different combinations constitute various alternative aspects of the invention.

What is claimed is:

1. A method of treating an eye with hyperopia comprising:
    a) measuring the refractive characteristics of the eye at the central and peripheral retina, comprising:
        i) measuring on-axis refractive error, and
        ii) measuring off-axis error at more than one field angle in the nasal and temporal directions, respectively;
    b) determining from said measuring that the eye has asymmetrical off-axis refractive characteristics; and
    c) affecting the refractive properties of an ocular system comprising the eye to provide clear or acceptable vision on-axis and to control the position of the image of peripheral objects to behind the retina so as to also reduce said asymmetry for at least one off-axis angle; said affecting comprising applying an orthokeratology lens to the eye or inserting a corneal implant into the eye, wherein the orthokeratology lens or the corneal implant provides said clear or acceptable vision on-axis and controls the position of the image of peripheral objects by reshaping the cornea;
    wherein the ocular system comprises the eye and the lens for the eye, the lens comprising:
        i) a central optic zone with a refractive power having a first power profile to correct on-axis vision of the eye so as to provide said clear or acceptable vision on-axis;
        ii) a nasal optic zone and a temporal optic zone, wherein:
            1) the nasal optic zone has a second power profile for controlling the position of the image of peripheral objects received on the nasal side of the retina; and
            2) the temporal optic zone has a third power profile for controlling the position of the image of peripheral objects received on the temporal side of the retina;
    wherein at least the second power profile is different from the third power profile so as to reduce said asymmetry;
    wherein the nasal optic zone and the temporal optic zone of said lens:
        i) refract light to be received by the peripheral retina so as to be focused on or behind the retina, and
        ii) have different refractive powers; and
    wherein the refractive power of the nasal optic zone or the temporal optic zone is selected to place peripheral images on the retina, and the refractive power of the other optic zone is selected to place peripheral images off the retina.

2. The method of claim 1, wherein the lens is a lens selected from the group comprising a contact lens.

3. The method of claim 1, wherein the step of affecting the refractive properties of an ocular system comprising the eye comprises applying the orthokeratology lens to the eye.

4. The method of claim 1, wherein the step of affecting the refractive properties of an ocular system comprising the eye comprises inserting the corneal implant into the eye.

5. The method of claim 1, wherein the nasal optic zone has an increased power relative to a power on-axis and the temporal optic zone has a decreased power relative to the power on-axis.

6. The method of claim 1, wherein the temporal optic zone has an increased power relative to an on-axis power and the nasal optic zone has a decreased power relative to the on-axis power.

7. The method of claim 1, wherein the lens further comprises:
    i) a stabilizing mechanism; and
    ii) a central optic zone between the nasal and the temporal optic zones, the central optic zone being asymmetrical about a vertical meridian through the lens, so as to extend across horizontal half meridians of the lens to different extents, wherein thevertical and horizontal meridians refer to the orientation of the lens caused by the stabilizing mechanism.

8. The method of claim 7, wherein the central optic zone includes a refractive power for correcting defocus.

9. The method of claim 1, wherein:
    i) the lens further comprises a stabilizing mechanism; and
    ii) the nasal optic zone and the temporal optic zone both include a substantially constant refractive power in a vertical direction, wherein the vertical direction is with reference to the orientation of the lens caused by the stabilizing mechanism.

10. The method of claim 1, wherein the nasal optic zone has a vertical height of between 0.5 mm and 3 mm and the temporal optic zone has a vertical height of between 0.5 mm and 3 mm.

11. The method of claim 10, wherein the lens has a refractive power substantially equal to the refractive power of the central optic zone above and below the nasal and temporal optic zones.

12. The method of claim 1, wherein the central optic zone is substantially rotationally symmetrical.

13. The method of claim 1, wherein the lens further comprises:
    i) a stabilizing mechanism; and
    ii) wherein the central optic zone is elongate in a vertical direction across the lens, and wherein the vertical direction is with reference to the orientation of the lens caused by the stabilizing mechanism.

14. The method of claim 13, wherein the lens is a contact lens with an optic zone and a carrier and wherein the central optic zone extends in the vertical direction across substantially the entire optic zone.

15. A method of treating an eye with hyperopia comprising:
    a) measuring the refractive characteristics of the eye at the central and peripheral retina, comprising:
        i) measuring on-axis refractive error, and
        ii) measuring off-axis error at more than one field angle in the nasal and temporal directions, respectively;
    b) determining from said measuring that the eye has asymmetrical off-axis refractive characteristics; and
    c) affecting the refractive properties of an ocular system comprising the eye to provide clear or acceptable vision on-axis and to control the position of the image of peripheral objects to behind the retina so as to also reduce said asymmetry for at least one off-axis angle; said affecting comprising applying a lens to the eye, wherein the lens comprises:
  i) a central optic zone with a refractive power to correct on-axis vision of the eye so as to provide said clear or acceptable vision on-axis;
  ii) a nasal optic zone and a temporal optic zone, wherein:
    1) the nasal optic zone controls the position of the image of peripheral objects received on the nasal side of the retina;
    2) the temporal optic zone controls the position of the image of peripheral objects received on the temporal side of the retina; and
    3) the nasal optic zone and the temporal optic zone refract light to be received by the peripheral retina so as to be focused on or behind the retina;
  wherein the nasal optic zone has an increased power relative to a power on-axis and the temporal optic zone has a decreased power relative to the power on-axis.

16. The method of claim 15, wherein the lens is a lens selected from the group comprising a contact lens and a spectacle lens.

17. The method of claim 16, wherein the lens further comprises a stabilizing mechanism.

18. The method of claim 17, wherein the central optic zone is asymmetrical about a vertical meridian through the lens, so as to extend across horizontalhalf meridians of the lens to different extents, wherein the vertical and horizontal meridians refer to the orientation of the lens caused by the stabilizing mechanism.

19. The method of claim 18, wherein the central optic zone is not plano and includes a refractive power for correcting defocus.

20. The method of claim 17, wherein the nasal optic zone and the temporal optic zone both include a substantially constant refractive power in a vertical direction, wherein the vertical direction is with reference to the orientation of the lens caused by the stabilizing mechanism.

21. The method of claim 17, wherein the central optic zone is elongate in a vertical direction across the lens, and wherein the vertical direction is with reference to the orientation of the lens caused by the stabilizing mechanism.

22. The method of claim 21, wherein the lens is a contact lens with an optic zone and a carrier and wherein the central optic zone extends in the vertical direction across substantially the entire optic zone.

23. The method of claim 15, wherein the nasal optic zone has a vertical height of between 0.5 mm and 3 mm and the temporal optic zone has a vertical height of between 0.5 mm and 3 mm.

24. The method of claim 23, wherein the lens has a refractive power substantially equal to the refractive power of the central optic zone above and below the nasal and temporal optic zones.

25. The method of claim 15, wherein the central optic zone is substantially rotationally symmetrical.

26. The method of claim 15, wherein the refractive power of the nasal optic zone or the temporal optic zone is selected to place peripheral images on the retina, and the refractive power of the other optic zone is selected to place peripheral images off the retina.

27. A method of treating an eye with hyperopia comprising:
  a) measuring the refractive characteristics of the eye at the central and peripheral retina, comprising:
    i) measuring on-axis refractive error, and
    ii) measuring off-axis error at more than one field angle in the nasal and temporal directions, respectively;
  b) determining from said measuring that the eye has asymmetrical off-axis refractive characteristics; and
  c) affecting the refractive properties of an ocular system comprising the eye to provide clear or acceptable vision on-axis and to control the position of the image of peripheral objects to behind the retina so as to also reduce said asymmetry for at least one off-axis angle; said affecting comprising applying a lens to the eye, wherein the lens comprises:
    i) a central optic zone with a refractive power to correct on-axis vision of the eye so as to provide said clear or acceptable vision on-axis;
    ii) a nasal optic zone and a temporal optic zone, wherein:
      1) the nasal optic zone controls the position of the image of peripheral objects received on the nasal side of the retina;
      2) the temporal optic zone controls the position of the image of peripheral objects received on the temporal side of the retina; and
      3) the nasal optic zone and the temporal optic zone refract light to be received by the peripheral retina so as to be focused on or behind the retina;
    wherein the temporal optic zone has an increased power relative to an on-axis power and the nasal optic zone has a decreased power relative to the on-axis power.

28. The method of claim 27, wherein the lens is a lens selected from the group comprising a contact lens and a spectacle lens.

29. The method of claim 28, wherein the lens further comprises a stabilizing mechanism.

30. The method of claim 29, wherein the central optic zone is asymmetrical about a vertical meridian through the lens, so as to extend across horizontal half meridians of the lens to different extents, wherein the vertical and horizontal meridians refer to the orientation of the lens caused by the stabilizing mechanism.

31. The method of claim 30, wherein the central optic zone is not plano and includes a refractive power for correcting defocus.

32. The method of claim 29, wherein the nasal optic zone and the temporal optic zone both include a substantially constant refractive power in a vertical direction, wherein the vertical direction is with reference to the orientation of the lens caused by the stabilizing mechanism.

33. The method of claim 29, wherein the central optic zone is elongate in a vertical direction across the lens, and wherein the vertical direction is with reference to the orientation of the lens caused by the stabilizing mechanism.

34. The method of claim 33, wherein the lens is a contact lens with an optic zone and a carrier and wherein the central optic zone extends in the vertical direction across substantially the entire optic zone.

35. The method of claim 27, wherein the nasal optic zone has a vertical height of between 0.5 mm and 3 mm and the temporal optic zone has a vertical height of between 0.5 mm and 3 mm.

36. The method of claim 35, wherein the lens has a refractive power substantially equal to the refractive power of the central optic zone above and below the nasal and temporal optic zones.

37. The method of claim 27, wherein the central optic zone is substantially rotationally symmetrical.

38. The method of claim 27, wherein the refractive power of the nasal optic zone or the temporal optic zone is selected to place peripheral images on the retina, and the refractive power of the other optic zone is selected to place peripheral images off the retina.

* * * * *